(12) United States Patent  (10) Patent No.: US 7,479,125 B2
Tashiro  (45) Date of Patent: Jan. 20, 2009

(54) BREAST PUMP

(75) Inventor: Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 73 days.

(21) Appl. No.: 10/522,876

(22) PCT Filed: Oct. 4, 2004

(86) PCT No.: PCT/JP2004/014596

§ 371 (c)(1),
(2), (4) Date: Feb. 2, 2005

(87) PCT Pub. No.: WO2005/042062

PCT Pub. Date: May 12, 2005

(65) Prior Publication Data

US 2005/0256449 A1 Nov. 17, 2005

(30) Foreign Application Priority Data

Oct. 30, 2003 (JP) ............................. 2003-370973

(51) Int. Cl.
A61M 1/06 (2006.01)
A61M 1/00 (2006.01)
(52) U.S. Cl. ........................................ 604/74; 604/313
(58) Field of Classification Search ............. 604/73–76, 604/313–316
See application file for complete search history.

(56) References Cited

U.S. PATENT DOCUMENTS 5,885,246 A * 3/1999 Ford ............................ 604/74
5,941,847 A * 8/1999 Huber et al. .................. 604/74
6,663,587 B2 * 12/2003 Silver et al. .................. 604/74
6,673,037 B1 * 1/2004 Silver .......................... 604/74
2003/0139702 A1 * 7/2003 Renz et al. .................. 604/74
2003/0153869 A1 * 8/2003 Ytteborg ..................... 604/74

* cited by examiner

Primary Examiner—Kevin C Sirmons
Assistant Examiner—Andrew M Gilbert
(74) Attorney, Agent, or Firm—Cermak Kenealy Vaidya & Nakajima LLP

(57) ABSTRACT

[Problem] To provide a breast pump capable of securely holding a breast of a user and intensively stimulating a particular potion of the breast.

[Means for Resolution] A breast pump 100 including a milk container main body 110; deformable means 170 for forming a sealed space; a horn member 150; space internal pressure altering means 190 for alternately providing a negative pressure condition and an atmospheric pressure condition in the sealed space; and a communicating portion 130, wherein: the horn member has a base end portion 151 disposed near the communicating portion and an opening end 152 disposed near an entrance through which the breast is inserted; the deformable means covers the inner surface of the horn member 150 and has a base end side attachable and detachable portion 171 to be fixed to the base end of the horn member and an opening side attachable and detachable portion 172 to be fixed to the opening end of the horn member; the deformable means has a stimulating convex 173 disposed between the base end side attachable and detachable portion and the opening side attachable and detachable portion; and the horn member has atmospheric pressure condition creating means for maintaining an atmospheric pressure condition in a space between the stimulating convex and the horn member.

21 Claims, 12 Drawing Sheets

BREAST PUMP

TECHNICAL FIELD

The present invention relates to an improvement of a breast pump such as a manual breast pump operated manually and an electrically-powered breast pump driven by a motor or other means, providing a breast pump capable of periodically varying suction pressure.

BACKGROUND ART

As a manual breast pump or other which includes a suction pump or other component operated by a user, a type having a deformable sucking portion has been proposed (see Patent Reference No. 1, for example). As illustrated in FIG. 1 of Patent Reference No. 1, a manual breast pump includes a large cup 41 made from elastic material to directly contact a breast of the user, and a shell 43 made from rigid material and disposed outside the large cup 41. When a suction pump 5 is operated with the large cup 41 attached to the breast of the user, negative pressure is generated within the large cup 41. Then, the large cup 41 made from elastic material is sucked toward the breast and thus presses the breast, thereby effectively sucking milk.

Patent Reference No. 1: JP-A-2002-85552 (FIG. 1 and others)

DISCLOSURE OF THE INVENTION

In the breast pump disclosed in Patent Reference No. 1, however, the entire body of the large cup 41 is deformed by the negative pressure described above. For efficiently sucking mother's milk, it is necessary to intensively stimulate the mammary areola and the adjoining region. Since the large cup 41 is entirely deformed, the conventional breast pump cannot intensively stimulate the particular area.

Additionally, in the periphery and other regions of the manual breast pump shown in Patent Reference No. 1, the rim of the large cup 41 is largely deformed when the negative pressure is produced inside the large cup 41 as described above. As a result, the user's breast cannot be securely held by the breast pump thus deformed.

In accordance with an aspect of the invention, a breast pump can include: a milk container main body capable of accommodating sucked mother's milk; deformable means for providing a sealed space by contacting a breast; a horn member disposed outside the deformable means; space internal pressure altering means for alternately providing a negative pressure condition and an atmospheric pressure condition in the sealed space; and a communicating portion for connecting the space internal pressure altering means and the sealed space, characterized in that: the horn member is not deformed when internal pressure within the sealed space varies and has a base end disposed near the communicating portion and an opening end disposed near an entrance through which the breast is inserted; the deformable means covers the inner surface of the horn member, deforms when internal pressure within the sealed space varies, and has an attachable and detachable portion which is attachable to and detachable from the horn member; the attachable and detachable portion has a base end side attachable and detachable portion to be fixed to the base end of the horn member and an opening side attachable and detachable portion to be fixed to the opening end of the horn member; the deformable means has a stimulating convex projecting inwardly; the stimulating convex is disposed between the base end side attachable and detachable portion and the opening side attachable and detachable portion; and the horn member has atmospheric pressure condition creating means for maintaining an atmospheric pressure condition in a space between the stimulating convex and the horn member.

According to another aspect of the invention, the breast pump includes the deformable means for providing a sealed space by contacting the breast, the horn member disposed outside the deformable means, and the space internal pressure altering means for alternately providing a negative pressure condition and an atmospheric pressure condition in the sealed space. The deformable means covers the inner surface of the horn member and deforms when the internal pressure in the sealed space varies.

Thus, the deformable means deforms to project toward the breast when negative pressure is created within the sealed space by the space internal pressure altering means. Then, when an atmospheric pressure condition is produced within the sealed space, the deformable means returns to the condition prior to the deformation.

The horn member is not deformed even when the internal pressure in the sealed space varies, and has the base end disposed near the communicating portion and the opening end disposed near the entrance through which the breast is inserted. The deformable means has the attachable and detachable portion which is attachable to and detachable from the horn member, and the attachable and detachable portion has the base end side attachable and detachable portion to be fixed to the base end of the horn member and the opening side attachable and detachable portion to be fixed to the opening end of the horn member.

The base end side attachable and detachable portion and the opening side attachable and detachable portion of the deformable means are disposed on the base end and the opening end, respectively, of the horn member which is not deformed even when the internal pressure in the sealed space varies.

The deformable means has the stimulating convex projecting inwardly and disposed between the base end side attachable and detachable portion and the opening side attachable and detachable portion.

Thus, when the deformable means is deformed by the space internal pressure altering means, an area of the deformable means between the base end side attachable and detachable portion and the opening side attachable and detachable portion deforms or exhibits other changes toward the breast. Since the stimulating convex is disposed in the area where the deformable means deforms, the stimulating convex intensively stimulates a particular portion such as mammary areola of the breast, thereby efficiently sucking mother's milk.

The base end side attachable and detachable portion and the opening side attachable and detachable portion of the deformable means are disposed on and fixed to the base end and the opening end, respectively, of the horn member which does not deform even when the internal pressure in the sealed space varies. Thus, the entire shape formed by the deformable means and the horn member is not greatly changed even when the intermediate portions and other area thereof are deformed. Accordingly, the situation that the breast of the user cannot be held securely due to the excessive deformation of the opening end, for example, can be prevented in advance.

More specifically, when the breast pump is pressed against the breast with the base end side attachable and detachable portion and the opening side attachable and detachable portion of the deformable means disposed on the horn member, the sealed space between the deformable means and the breast is securely sealed due to the rigidity of the horn member. Additionally, the intermediate portion of the deformable means is deformable as the intermediate portion is not fixed to the horn member.

Accordingly, it is possible to simultaneously meet both the requirements for the easily deformable structure to stimulate the breast for sucking and for the rigid structure difficult to deform for contacting the breast and avoiding breakage of the sealed space.

The horn member has atmospheric pressure condition creating means for maintaining an atmospheric pressure condition in a space between the stimulating convex and the horn member.

More specifically, since the horn member disposed outside the deformable means is not deformed by the space internal pressure altering means, negative pressure and the like is generated in a space between the horn member and the area of the deformable means where the stimulating convex is provided, for example. As a result, the deformation of the deformable means may be prevented by the horn member. In this aspect, the atmospheric pressure condition creating means is provided on the horn member so as to maintain an atmospheric pressure condition in the space between the stimulating convex and the horn member in this claim of the invention. Accordingly, the deformation or other change of the deformable means due to the negative pressure created in the sealed space is not prevented but is smoothly achieved, thereby allowing more efficient sucking to be performed.

In accordance with another aspect of the invention is a breast pump can be characterized in that the stimulating convex of the deformable means is disposed in the vicinity of a curvature altering portion where a curvature of the base end of the horn member alters.

According to this aspect of the invention, the stimulating convex of the deformable means is disposed in the vicinity of the curvature altering portion where the curvature of the base end of the horn member alters.

Since the mammary areola and the adjoining region of the breast is positioned in the vicinity of the curvature altering portion where the curvature of the base end of the horn member alters when the breast of the user is attached, the mammary areola and the adjoining region of the breast which are to be stimulated most for efficient sucking of milk can be intensively stimulated by the stimulating convex.

As a result, mother's milk is more easily and effectively sucked.

According to another aspect of the invention a breast pump can be characterized in that the base end side attachable and detachable portion of the deformable means is disposed between the communicating portion and the base end of the horn member.

According to the this aspect of the invention, the base end side attachable and detachable portion of the deformable means is disposed between the communicating portion and the base end of the horn member. Thus, the base end side attachable and detachable portion is easily disposed by inserting the base end side attachable and detachable portion between the communicating portion and the horn member. Accordingly, the base end side attachable and detachable portion can be easily and securely disposed and fixed without requiring a complicated structure, and the deformable means is prevented from separating from the horn member when the deformable means deforms due to fluctuation in negative pressure produced within the sealed space.

According to another aspect of the invention, a breast pump can be characterized in that the atmospheric pressure condition creating means is a vent opening for connecting a space between the horn member and the deformable means with the outside.

According to this aspect of the invention, since the atmospheric pressure condition creating means is a vent opening for connecting the space between the horn member and the deformable means with the outside, the atmospheric pressure condition creating means can be easily manufactured at low cost.

According to another aspect of the invention, a breast pump can be characterized in that a deformation guide portion for regulating a deformation direction of the deformable means is provided on the deformable means.

According to this aspect of the invention, since the deformation direction of the deformable means is regulated by the deformation guide portion of the deformable means, the deformable means can be made to deform in a direction where the stimulating convex intensively contacts the mammary areola and other regions of the breast, for example. Accordingly, the breast can be effectively stimulated by the breast pump.

According to another aspect of the invention, a breast pump can be characterized in that: the stimulating convex is provided at a plurality of positions within the deformable means, and at least some of these stimulating convexes are opposed to each other on a first virtual line; and the deformation guide portion is disposed on a second virtual line which crosses the first virtual line.

According to this aspect of the invention, the plural stimulating convexes are opposed to each other on the first virtual line, and the deformation guide portion is disposed on the second virtual line which crosses the first virtual line.

Thus, the deformable means is deformed in a direction where the stimulating convexes which are disposed on the deformable means in such positions as to be opposed to each other approach each other by provision of the deformation guide portion.

At this stage, the stimulating convexes approaching each other intensively stimulate the mammary areola and other regions positioned within the deformable means from two directions such as from above and below.

This condition is similar to the condition where a baby and others take a nipple of a mother into their mouths to suck milk. More specifically, a baby and others press a nipple of a mother by inserting the nipple between their tongues and the upper palates or other area within their mouths to peristaltically move the tongues. That is, a baby and others stimulate the nipple and other area from two directions such as from above and below.

Since the stimulating convexes stimulate the mammary areola and other region from two directions with respect to the nipple in this invention, the stimulating convexes act similarly to the real motion of a baby and others for sucking milk. Accordingly, the breast can be more efficiently stimulated by the breast pump.

In accordance with yet another aspect of the invention, a breast pump capable of securely holding a breast of a user and intensively stimulating a particular region of the breast.

DETAILED DESCRIPTION OF PREFERRED EMBODIMENTS

Preferred embodiments according to the present invention are hereinafter described in detail with reference to the appended drawings.

Various features and technical aspects are given to the embodiments described herein as they are specific examples of the invention. However, the scope of the invention is not limited to the embodiments.

Embodiment 1

FIG. 1 is a perspective view schematically illustrating a manual breast pump 100 in a first embodiment according to the present invention, and FIG. 2 is a schematic cross-sectional view of the manual breast pump 100 in FIG. 1.

As illustrated in FIG. 1, the manual breast pump 100 has a milk container main body for accommodating sucked milk such as a milk bottle 110. The milk bottle 110 is made from glass or plastic resin such as PES (polyethersulfone), polycarbonate and polypropylene.

A communicating portion 130 is provided in the vicinity of an opening (in the upper region) of the milk bottle 110 in such a position as to cover the opening of the milk bottle 110. The communicating portion 130 has a first opening S1 disposed in the upper right, a second opening S2 in the lower region, and a third opening S3 in the upper left in FIG. 2.

A first vent passage U1 is formed between the first opening S1 and the second opening S2, and a second vent passage U2 is formed between the second opening S2 and the third opening S3. A valve 200 is provided in such a position as to cover the second opening S2 as shown in FIG. 2.

The valve 200 has a slit 201 for allowing the valve 200 to open to the milk bottle 110 so that sucked mother's milk can pass through the slit 201 to fall into the milk bottle 110. The valve 200 is not limited to the type shown in FIG. 2 but may be other type as long as it can separate air in the milk bottle and air in the communicating portion 130 at the time of sucking. Alternatively, the valve may be eliminated.

Deformable means such as a deformable member 170 with which the breast of a user contacts and a horn-shaped portion such as a horn member 150 disposed outside the deformable member 170 are provided near the first opening S1. The horn member 150 is a bowl-shaped component as illustrated in FIG. 1.

FIG. 3 is a partial enlarged view of FIG. 2. The horn member 150 in FIG. 3 is made from a rigid material such as polycarbonate, PES, polypropylene, polyamide, polycycloolefin and other resins, and has a structure not easily deformed.

As illustrated in FIG. 3, an accommodating portion 132 which is connecting means for accommodating the deformable member 170 and the horn member 150 and attaching those to the communicating portion 130 is provided at the first opening S1 of the communicating portion 130. The accommodating portion 132 in a region close to the first opening S1 of the communicating portion 130 has a larger diameter to extend outwardly as shown in the figure.

The horn member 150 has a base end such as a horn base end portion 151 which is disposed near the accommodating portion 132 of the communicating portion 130. As illustrated in FIG. 3, the horn base end portion 151 has a base end side deformable member positioning portion 151b for positioning a base end side attachable and detachable portion of the deformable member 170 such as a base end side detachable and attachable portion 171 (to be described later) which is sandwiched between the horn base end portion 151 and the accommodating portion 132. When the base end side detachable and attachable portion 171 is disposed at the base end side deformable member positioning portion 151b as shown in FIG. 3 and then the horn member 150 is accommodated in the accommodating portion 132 of the communicating portion 130 as shown in FIG. 2, the base end side detachable and attachable portion 171 of the deformable member 170 comes to be positioned between the horn member 150 and the communicating portion 130.

Thus, the base end side detachable and attachable portion 171 is sandwiched between the horn member 150 and the communicating portion 130 to be fixed therein. This fixation only requires the base end side detachable and attachable portion 171 to be positioned at the base end side deformable member positioning portion 151b and then accommodated in the accommodating portion 132 of the communicating portion 130, and thus an easy and reliable fixing structure can be realized.

Additionally, the horn base end portion 151 has a positioning convex 151a for positioning the horn member 150 which is attached to the accommodating portion 132 of the communicating portion 130. The horn member 150 is positioned by the positioning convex 151a which contacts the end of the accommodating portion 132 of the communicating portion 130.

The horn member 150 has an opening end such as a horn opening portion 152 disposed in the right region in FIG. 3. Since the user inserts the breast through the horn opening portion 152, the horn opening portion 152 is located at an entrance through which the breast is inserted.

The deformable member 170 shown in FIGS. 1 and 3 and other figures is made from elastic material such as silicone rubber, elastomer and isoprene rubber. The base end side detachable and attachable portion 171 which is fixed to the horn base end portion 151 of the horn member 150 is formed on the deformable member 170 near the communicating portion 130. The base end side detachable and attachable portion 171 is inserted into the communicating portion 130 to be fixed therein as described above. Thus, the base end side detachable and attachable portion 171 functions as a packing which securely seals the clearance between the communicating portion 130 and the horn member 150.

An opening side attachable and detachable portion such as an opening side detachable and attachable portion 172 which is fixed to the horn opening portion 152 of the horn member 150 is formed on the deformable member 170 near the opening thereof (in the right region in FIG. 3). More specifically, the opening side detachable and attachable portion 172 is provided in such a position as to cover the entire circumference of the horn opening portion 152, whereby the opening side detachable and attachable portion 172 is fixed thereon and prevented from being separated therefrom easily as illustrated in FIG. 3. The opening side detachable and attachable portion 172 is an area which is pushed against the breast at the time of sucking. Thus, the opening side detachable and attachable portion 172 scarcely comes off during use, and may be fixed with smaller fixing force than that for fixing the base end side detachable and attachable portion 171 or may be partially provided on the horn opening portion 152 rather than on its entire circumference.

Accordingly, the deformable member 170 is fixed to the horn member 150 at the two points of the base end side detachable and attachable portion 171 and the opening side detachable and attachable portion 172, and the region between the two fixed positions is not fixed to the horn member 150.

For detaching the deformable member 170 thus disposed, the base end side detaching and attaching member 171 can be easily removed by separating the horn member 150 from the accommodating portion 132 of the communicating portion 130. The opening side detachable and attachable portion 172 can be easily detached by the user's hand since the deformable member 170 is a flexible component.

Thus, the deformable member 170 can be easily attached to and detached from the horn member 150.

As illustrated in FIG. 3, the deformable member 170 has four, for example, stimulating convexes 173 projecting inwardly and formed between the base end side detachable and attachable portion 171 and the opening side detachable and attachable portion 172. The stimulating convexes 173 are disposed in the vicinity of a curvature altering portion 154 where the curvature of the horn base end portion 151 of the horn member 150 alters. The stimulating convexes 173 curve at the positions of outer surface portions 173a and project out from the flat surface of the deformable member 170, allowing the outer surface portions 173a and the stimulating convexes 173 to be easily deformed in accordance with the deformation of the deformable member 170.

The stimulating convexes 173 are disposed at the four points opposed one another vertically and horizontally in FIG. 3, but may be obliquely positioned by rotating the stimulating convexes 173 through 45 degrees.

FIG. 4 schematically illustrates how mother's milk is produced in the human breast. As shown in this figure, the production and secretion of milk can be promoted by intensively pressing the mammary areola from outside to stimulate that portion.

The mammary areola is located in the vicinity of the curvature altering portion 154 shown in FIG. 3 when the breast is inserted into the deformable member 170 shown in FIG. 2 by the user. Thus, when negative pressure is generated by the action of negative pressure generating means 190 to be described later, the deformable member 170, especially the stimulating convexes 173 project inwardly, i.e., toward the breast. At this time, the mammary areola of the breast is stimulated and the production of milk is thus promoted.

Additionally, the horn member 150 has atmospheric pressure condition creating means such as four vent openings 153 at positions corresponding to the stimulating convexes 173.

More specifically, when the space between the deformable member 170 and the horn member 150 is sealed in the structure where the negative pressure generating means 190 generates negative pressure to deform the deformable member 170 so that the deformable member 170 projects toward the breast as described above, negative pressure and the like produced in that sealed space prevents the inward deformation of the deformable member 170. However, if atmospheric pressure is maintained in the space between the horn member 150 and the stimulating convexes 173 of the deformable member 170, negative pressure and the like are not generated therein and thus the actions of the stimulating convexes 173 are not prevented.

Since the deformation of the stimulating convexes 173 is not hindered, the mammary areola is more effectively stimulated and secretion of milk is more promoted.

Space internal pressure altering means such as the negative pressure generating means 190 is provided near the third opening S3 shown in FIG. 2 in such a position as to cover the third opening S3. The negative pressure generating means 190 has a lever 191 which is held and operated by the user as shown in FIG. 2. The negative pressure generating means 190 also has a piston guide 192 inside of which a packing 131a at the tip of a fixed piston 131 formed integrally with the communicating portion 130 slides.

A leaf spring 210 is disposed between the lever 191 and the communicating portion 130 shown in FIG. 2, which lever urges the negative pressure generating means 190 in a direction indicated by an arrow A1 in FIG. 2. The negative pressure generating means 190 also has pressure regulating means 194 for regulating pressure within the first vent passage U1 and the second vent passage U2 shown in FIG. 2.

When the breast is inserted from the deformable member 170 side to bring the breast into contact with the deformable member 170, the first vent passage U1 and the second vent passage U2 shown in FIG. 2 are sealed by the breast.

In this condition, the user shifts the lever 191 in a direction indicated by an arrow B1 in FIG. 2 while resisting the urging force of the leaf spring 210. FIG. 5 schematically illustrates the condition in which the lever 191 shown in FIG. 2 is shifted in the direction of the arrow B1 during sucking.

As illustrated in FIG. 5, negative pressure is generated in the vent passages U1 and U2, thereby establishing a pressure differential between the pressure in those passages and the atmospheric pressure. Thus, the communication portion 130 connects the sealed space between the negative pressure generating means 190 and the deformable member 170 where the breast is positioned.

Since the horn member 150 shown in FIG. 5 is made from highly rigid material, the horn member 150 is not deformed by the negative pressure. On the other hand, since an area of the deformable member 170 between the base end side detachable and attachable portion 171 and the opening side detachable and attachable portion 172, which area is not fixed to the horn member 150, is made from flexible material, that area of the deformable member 170 is deformed inwardly as illustrated in FIG. 5.

Especially, as the pressure in the space between the horn member 150 and the deformable member 170 is kept equal to the atmospheric pressure in the regions where the vent openings 153 of the horn member 150 are formed, those regions are positively deformed with no force for preventing the deformation applied thereto.

As described above, since the stimulating convexes 173 are disposed in the regions which are to be securely deformed as shown in FIG. 5, the area in the vicinity of the mammary areola of the user can be intensively stimulated as described above, thereby promoting production of mother's milk more effectively for enhanced sucking operation.

While negative pressure is generated by the negative pressure generating means 190 and thus the deformable member 170 is deformed, the base end side detachable and attachable portion 171 and the opening side detachable and attachable portion 172 are fixed to the horn member 150 which is not deformed. Especially, the base end side detachable and attachable portion 171 which is inserted to be fixed does not move to come off by the deformation. Accordingly, the condition that the opening side detachable and attachable portion 172 or other portion is deformed too much to hold the breast of the user can be avoided in advance. More specifically, when the breast is attached to the breast pump 100, the space between the deformable member 170 and the breast can be securely sealed by the rigidity of the horn member 150 as the opening side detachable and attachable portion 172 and the base end side detachable and attachable portion 171 are fixed to the horn member 150.

On the other hand, as the region between the opening side detachable and attachable portion 172 and the base end side detachable and attachable portion 171 of the deformable member 170 is not fixed to the horn member 150 and is thus easily deformed, the breast can be stimulated at required positions. Accordingly, in this embodiment as described above, it is possible to simultaneously meet both the requirements for the easily deformable structure to stimulate the breast for the efficient sucking and for the rigid structure difficult to deform for contacting the breast and avoiding breakage of the sealed space.

When the negative pressure generating means 190 shown in FIG. 5 is further shifted in the direction indicated by the arrow B1, the condition shown in FIG. 6 is established. FIG. 6 schematically illustrates an air leak condition.

As shown in FIG. 6, the packing 131a at the tip of the fixed piston 131 of the communicating portion 130 reaches a leak tip 193 of the piston guide 192 of the negative pressure generating means 190. At this stage, a clearance between the packing 131a and the negative pressure generating means 190 is produced and the sealed conditions in the second vent passage U2 and the first vent passage U1 are broken, allowing the negative pressure to be equivalent to the atmospheric pressure. Then, the stimulating convexes 173 having stimulated the breast to promote the production of milk are separated from the breast.

At this stage, mother's milk secreted and sucked from the mammary papilla opens slit 201 of the valve 200 by its own weight to fall into the milk bottle 110.

Then, the user loosens the lever 191 which has been pressed to shift the negative pressure generating means 190 again in the direction indicated by the arrow A1 by the urging force of the leaf spring 210, whereby the space between the packing 131a and the piston guide 192 is sealed to establish the condition in FIG. 2. Accordingly, the manual breast pump 100 can achieve pulsation sucking by manipulation of the lever 191.

Since openings as the vent openings 153 are formed on the horn member 150 and the stimulating convexes 173 are disposed in the positions corresponding to the vent openings 153 as illustrated in FIG. 2 or other figures, the manual breast pump 100 has a simple structure and is manufactured at low cost and easily manipulated.

Example Modified from Embodiment 1

FIG. 7 schematically illustrates a manual breast pump 400 in an example modified from the first embodiment. Since many structures included in the manual breast pump 400 in this example are similar to those of the manual breast pump 100 in the first embodiment, reference numbers and the like similar to those in the first embodiment are given to the similar structures and the description of those is omitted. The modified example is now described while putting emphasis on its different points from the first embodiment.

As illustrated in FIG. 7, a stimulating convex 473 is formed only on one side, a side beneath the breast in this figure, for example, of a deformable member 470 in this modified example. A vent opening 453 is disposed only on a lower side of a horn member 450 in correspondence with the stimulating convex 473. When the breast is brought into contact with the deformable member 470 as illustrated in FIG. 7, production of mother's milk can be effectively promoted even by stimulating only the lower side of the mammary areola using the stimulating convex 473.

According to this example in which the stimulating convex 473 is formed only on the lower side, it is possible to give a mother a feeling similar to sucking by a baby in which rise of the tongue peristaltically moves with suction pressure as the negative pressure generated.

Additionally, this example is different from the first embodiment in the structure of the connecting means formed by the accommodating portion 132 of the communicating portion 130, the base end side deformable member positioning portion 151b of the horn member 150 and the base end side detachable and attachable portion 171 of the deformable member 170.

As illustrated in FIG. 7, a base end side detachable and attachable portion 471 attached to the base end side deformable member positioning portion 451b is press-fitted such that the base end side detachable and attachable portion 471 covers connecting means 432 as an accommodating portion. More specifically, not only the base end side detachable and attachable portion 471 but also a detaching and attaching region of the deformable member 470 is sandwiched between the connecting means 432 and the base end side deformable member positioning portion 451b so as to securely fix the deformable member 470 without separation thereof. Since the connecting means 432 is disposed at an inner position from the deformable member 470, the inside surface of the connecting means 432 is curved so as not to stimulate the breast by its edges.

Embodiment 2

FIG. 8 schematically illustrates a main part of a manual breast pump 300 in a second embodiment according to the invention. Since many structures included in the manual breast pump 300 in FIG. 8 are similar to those of the manual breast pump 100 in the first embodiment, reference numbers and the like similar to those in the first embodiment are given to the similar structures and the description of those is omitted. The second embodiment is now described while putting emphasis on its different points from the first embodiment.

As illustrated in FIG. 8, the second embodiment is different from the first embodiment in that the horn member and the communicating portion are not separated but formed as a communicating portion 330 including the horn member. That is, the communicating portion 130 and the horn member 150 in the first embodiment are formed as the one-piece communicating portion 330 which has a horn area to be attached to the breast.

The communicating portion 330 has a hole 331 for attaching and detaching the base end side of the deformable member 370. The hole 331 for attaching and detaching the base end side is a round penetration into which a base end side attachable and detachable portion 372 formed on the deformable member 370 is inserted. Since the base end side attachable and detachable portion 372 is a round convex which is slightly larger than the hole 331 for attaching and detaching the base end side, the base end side attachable and detachable portion 372 can be fixed thereto.

Accordingly, unlike the first embodiment, a holding member for detachably fixing the base end side of the deformable member 370 to the communicating portion 330 as the one-piece component of the horn member and the communicating portion is provided so as to secure the deformable member 370 in this embodiment.

The base end side attachable and detachable portion 372 or other component as the holding means may be provided on the horn member 150 and the communicating portion 130 as separated components in the first embodiment.

Furthermore, this embodiment is different from the first embodiment in that the thickness of stimulating convexes 373 formed on the deformable member 370 is increased. More specifically, since the cross section of the stimulating convexes 373 is substantially semicircular as illustrated in FIG. 8, the stimulating convexes 373 can offer strong stimulation. Vent openings 353 are formed in the positions corresponding to the stimulating convexes 373 similarly to the first embodiment. Alternatively, the stimulating convexes 373 may have a thinner-wall structure so as to be more deformable.

According to the manual breast pump 300 in this embodiment, the number of the components included therein is not increased since the communicating portion and the horn member are formed as a one-piece component, and strong stimulation can be provided by means of the stimulating convexes 373 during sucking.

Embodiment 3

FIG. 9 schematically illustrates a manual breast pump 500 in a third embodiment according to the invention. Since many structures included in the manual breast pump 500 in this embodiment are similar to those of the manual breast pump 100 in the first embodiment, reference numbers and the like similar to those in the first embodiment are given to the similar structures and the description of those is omitted. The third embodiment is now described while putting emphasis on its different points from the first embodiment.

This embodiment is different from the first embodiment in that the communicating portion and the horn member are formed as a one-piece communicating portion 530 which has a horn area to be attached to the breast. Vent openings are not provided on the communicating portion 530, and vent openings 553 are formed between a horn opening portion 552 of the communication portion 530 and an opening side attachable and detachable portion 572 of a deformable member 570 as illustrated in FIG. 9. More specifically, the groove-shaped vent openings 553 extend from three stimulating convexes 573 of the deformable member 570 in this embodiment toward the opening through which the breast is inserted such that the grooves surround the horn opening portion 552, whereby the stimulating convexes 573 communicate with the outside air. As shown in the upper region of the figure, the deformable member 570 is disposed in such a position as to cover the horn opening portion 552 in an area other than the vent openings 553 so as to be also fixed at the opening.

Thus, the vent openings 553 shown in FIG. 9 function as an example of atmospheric pressure condition creating means for maintaining an atmospheric pressure condition in the area between the deformable member 570 and the communicating portion 530.

There is no convex and concave engagement between a base end side detachable and attachable portion 571 of the deformable member 570 and the communicating portion 530, and those components are fixed to each other by frictional force generated by a large contacting area therebetween or by press-fitting the base end side detachable and attachable portion 571 of the deformable member 570 having slightly larger outside diameter than the inside diameter of the communicating portion 530 into the communicating portion 530.

In this embodiment, only the deformable member 570 is required to be prepared and attached to a horn-shaped component of an existing breast pump before use as no special structure is included in the communicating portion 530. Moreover, the manual breast pump 500 can be used when the sizes of the breast and the mammary areola vary and thus the breast cannot be positioned in the communicating portion 530.

Embodiment 4

FIG. 10 schematically illustrates an electrically-powered breast pump 600 in a fourth embodiment according to the invention. Since many structures included in the manual breast pump 600 in this embodiment are similar to those of the manual breast pump 100 in the first embodiment, reference numbers and the like similar to those in the first embodiment are given to the similar structures and the description of those is omitted. The fourth embodiment is now described while putting emphasis on its different points from the first embodiment.

As illustrated in FIG. 10, the electrically-powered breast pump 600 includes a pump unit 610 and bottle holders 620 disposed in the vicinity of both sides of the pump unit 610. The pump unit 610 is a component for driving the pump using a motor or other means, and is employed in lieu of the negative pressure generating means 170 shown in FIG. 1. More specifically, negative pressure is manually produced within the communicating portion 130 and the deformable member 170 in the first embodiment, but is generated by means of the electrically-powered pump in this embodiment.

A bottle unit 650 having the milk bottle 110, the deformable member 170 and the horn member 150 is disposed in each of the bottle holders 620. While the milk bottle 110, the deformable member 170 and the horn member 150 included in the bottle unit 650 are the same as those in the first embodiment, a communicating portion 630 is slightly different. More specifically, since the suction force as the negative pressure is supplied from the pump unit 610, the bottle units 650 are connected to the pump unit 610 through suction tubes 640 as illustrated in FIG. 10.

The pump unit 610 has a power source switch 610a, suction controlling dial 610b and others.

For the electrically-powered breast pump capable of periodically varying negative pressure of this type, not only the structure in the first embodiment but also the structure in any of other embodiments may be adopted.

Also in this embodiment, negative pressure is generated by the pump unit 610, and the mammary areola of the breast is intensively stimulated by means of the stimulating convexes 173 of the deformable member 170. As a result, secretion of milk is promoted and thus efficient sucking is attained. Especially, since negative pressure is produced more efficiently by means which is not manual but electrically powered in this embodiment, the labor required for a mother or others as the user can be reduced.

Embodiment 5

FIG. 11 is a perspective view schematically illustrating a structure including a horn member 750, a deformable member 770 and other components as a main part of a manual breast pump 700 in a fifth embodiment according to the invention. FIG. 12 is a cross-sectional view schematically illustrating the horn member 750, the deformable member 770 and other components shown in FIG. 11. FIG. 13 is a schematic cross-sectional view of FIG. 12 taken along a line A-A' in FIG. 12.

Since many structures included in the manual breast pump 700 in this embodiment are similar to those of the manual breast pump 100 in the first embodiment, reference numbers and the like similar to those in the first embodiment are given to the similar structures and the description of those is omitted. The fifth embodiment is now described while putting emphasis on its different points from the first embodiment.

As illustrated in FIG. 12, an opening side detachable and attachable portion 772 of a deformable member 770 is provided in such a position as to cover a horn opening portion 752 as a horn opening end of the horn member 750 similarly to the third embodiment. A vent opening 753 is provided between the horn opening portion 752 and the opening side detachable and attachable portion 772.

Thus, an atmospheric pressure condition is maintained in the space between the horn member 750 and the deformable member 770 through the vent opening 753 shown in FIG. 12.

The breast pump 700 operates in this condition. When negative pressure is generated within the deformable member 770, the space between the deformable member 770 and the horn member 750 is brought into an atmospheric pressure condition by the air flow introduced through the vent opening 753. Since negative pressure is not created in that space, the actions of stimulating convexes 773 shown in FIG. 12 are not prevented due to negative pressure similarly to the third embodiment.

Accordingly, the stimulating convexes 773 disposed only vertically can intensively stimulate the mammary areola and other areas of the user.

In this embodiment shown in FIGS. 11, 12 and 13, deformation guide portions 778 for regulating the deformation direction of the deformable member 770 are provided on the deformable member 770.

The deformation guide portions 778 are fragile regions having thinner walls than other areas as illustrated in FIG. 13, for example, and have substantially the same length as that of the stimulating convexes 773.

As illustrated in FIG. 11 and other figures, each of the stimulating convexes 773 is formed at two points of the deformable member 770 vertically in the figure in such positions as to be opposed to each other on a first virtual line K1. The two deformation guide portions 778 are disposed on a second virtual line K2 which crosses the first virtual line K1 at right angles, for example, in such positions as to be opposed to each other.

In this embodiment, the two deformation guide portions 778 are oblong (indicated by a broken line in FIG. 11), for example.

In the manual breast pump 700 having the above structure according to this embodiment, when the breast is positioned in the deformable member 770 and the breast pump 700 is operated to generate negative pressure within the deformable member 770, the deformable member 770 deforms most greatly at the positions corresponding to the deformation guide portions 778 shown in FIG. 13.

By this deformation, the two stimulating convexes 773 shown in FIG. 13 positively approach each other (in directions indicated by arrows in FIG. 13). Since the mammary areola and other area of the user are disposed between the two stimulating convexes 773 as illustrated in FIG. 12, the two stimulating convexes 773 press the mammary areola and other area or give other actions thereto from above and below to intensively stimulate those regions. Thus, the movement of the two stimulating convexes 773 is restricted to the vertical direction by the deformation guide portions 778.

When a baby and others take a mammary areola and a nipple of a mother into their mouths to suck milk, they press the nipple taken into the mouths by inserting the nipple between their tongues and their upper palates or other area to peristaltically move the tongues. That is, a baby and others stimulate the nipple and other area from above and below.

Accordingly, the structure in which the stimulating convexes 773 intensively stimulate the mammary areola and other area from both above and below the nipple and other area in this embodiment is similar to a real sucking motion of a baby and others, and thus attains efficient stimulation given to the breast.

Since the two stimulating convexes 773 are oblong ellipses as illustrated in FIG. 11, the longitudinal direction of the stimulating convexes 773 is disposed along a direction from the tip to the root of the breast when the breast of the user is positioned in the deformable member 770.

It is known that a baby and others move their tongues from the tip to the root of a nipple of a mother or others during peristaltic motion of the tongue for sucking milk. Since the stimulating convexes 773 are oblong in the same direction as the moving direction of the tongue, the manual breast pump 700 is allowed to act in a similar manner to the real motion of the tongues of a baby and others.

The deformation guide portions 778 are oblong and have thinner walls in this embodiment as illustrated in FIG. 13, but may be grooves in the shape of slits or have other shapes having thinner walls. Additionally, the deformation guide portions may have shapes easily bended such as crank shapes formed on the deformable member 770 rather than the thinwall shapes. The stimulating convexes 773 during use as described above are vertically disposed, but the deformable member 770 may be attached such that the stimulating convexes 773 are horizontally disposed depending on users.

The cross-sections of the horn member 750 and the deformable member 770 and other regions where the stimulating convexes 773 are disposed may have elliptical or oblong shapes having a larger length in a lateral direction than in this embodiment. In this condition, the right and left sides of the deformable member 770 as viewed in FIG. 13 are easily bended when negative pressure is created within the deformable member 770 and the deformable member 770 is thus deformed. As a result, the right and left sides of the elliptical shape or other shapes are allowed to function as the deformation guide portions.

The present invention is not limited to the respective embodiments shown herein. Those embodiments may be combined to provide structures other than the described examples.

Figure 1:
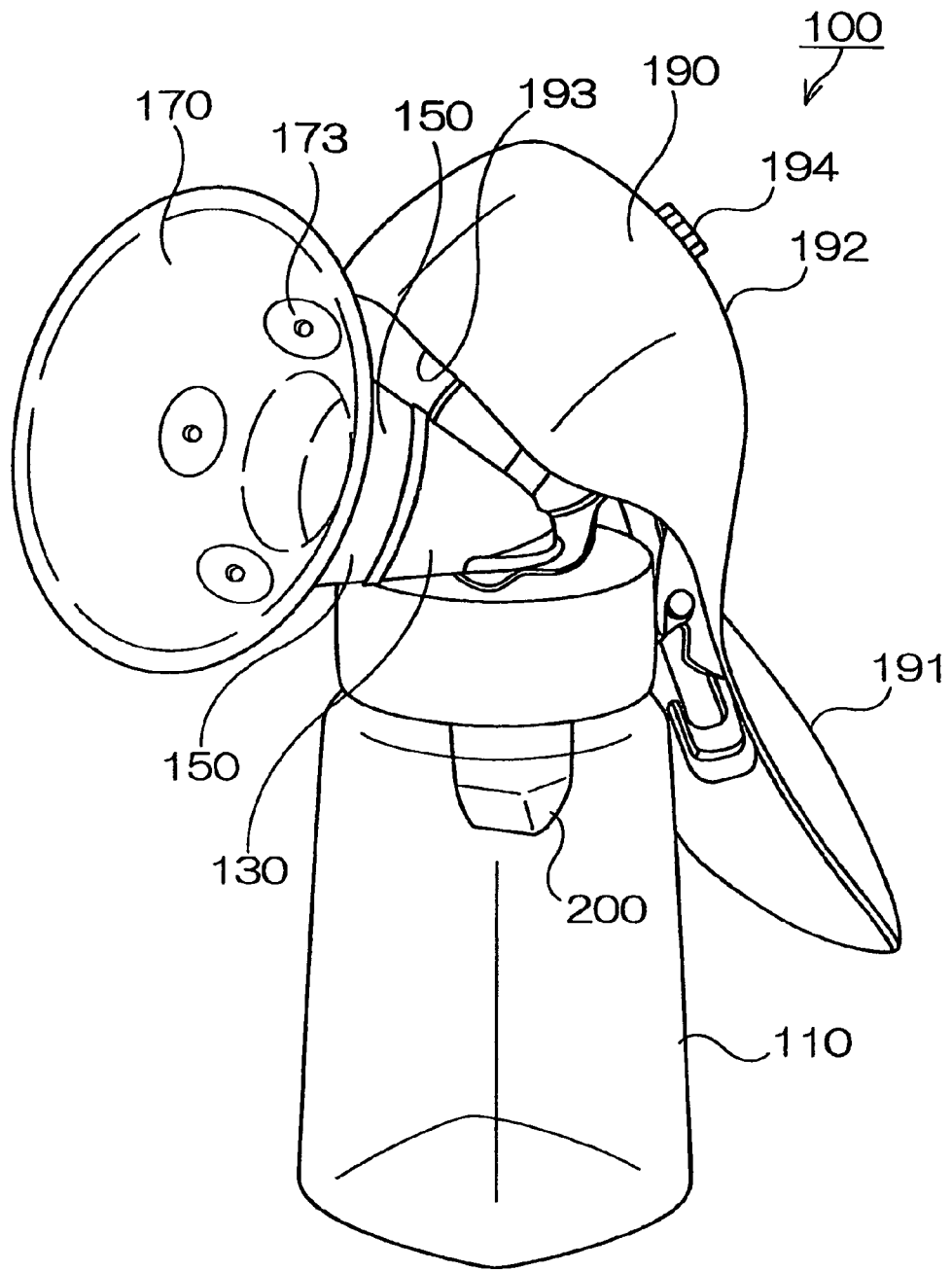
FIG. 1 is a perspective view schematically illustrating a manual breast pump in a first embodiment according to the present invention.
Figure 2:
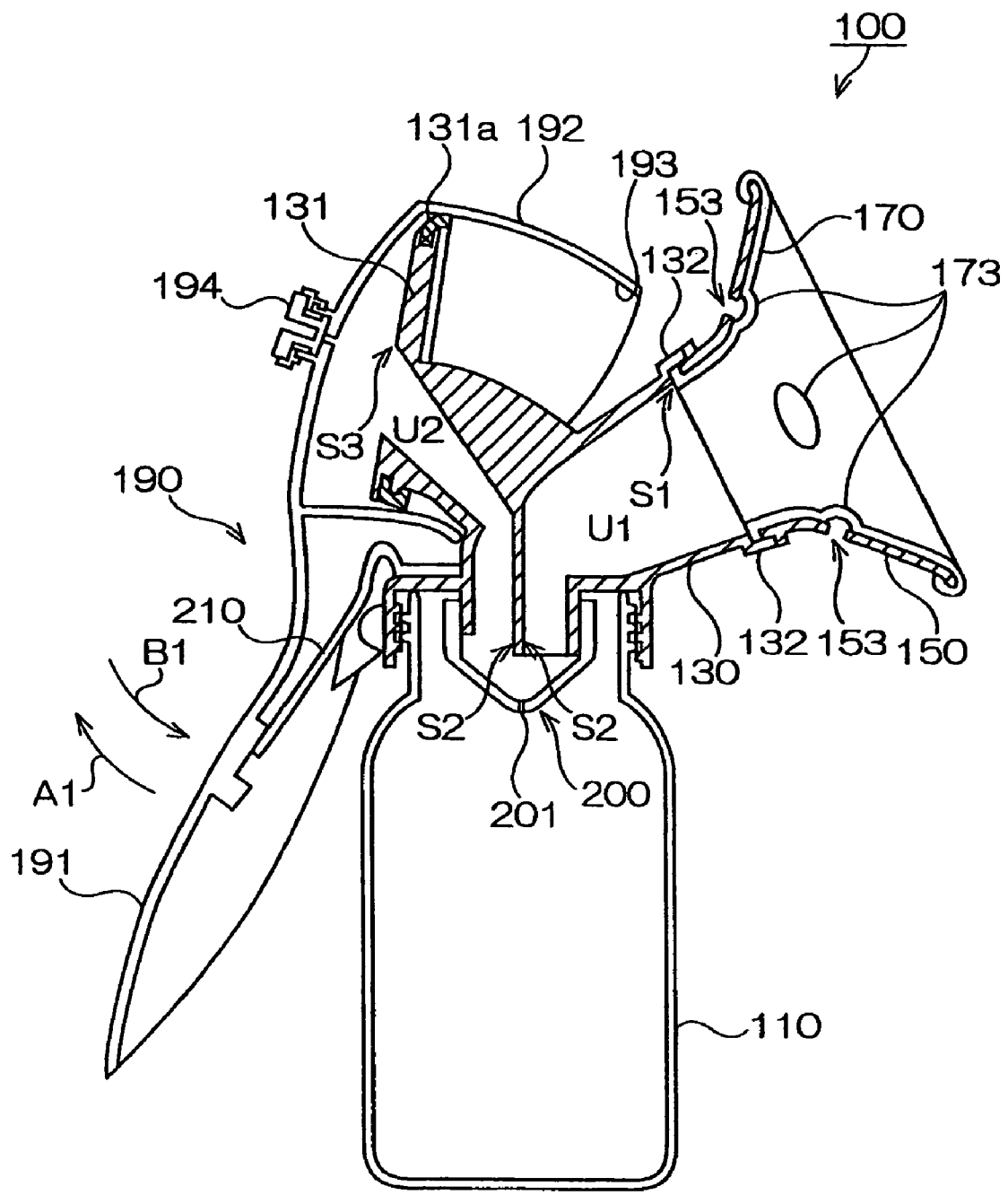
FIG. 2 is a cross-sectional view schematically illustrating the manual breast pump shown in FIG. 1.
Figure 3:
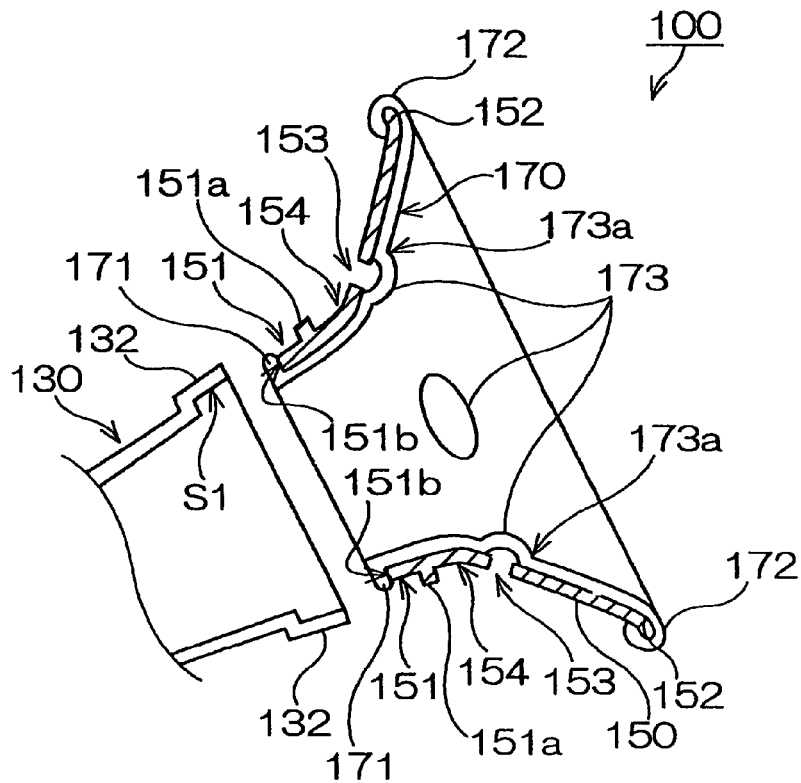
FIG. 3 is a partial enlarged view of FIG. 2.
Figure 4:
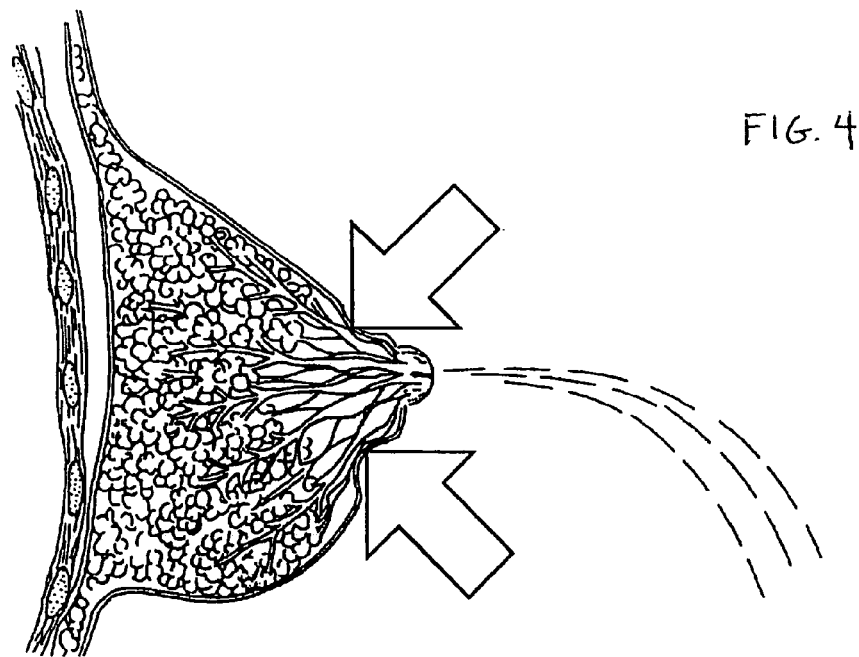
FIG. 4 schematically illustrates production of mother's milk in a human breast.
Figure 5:
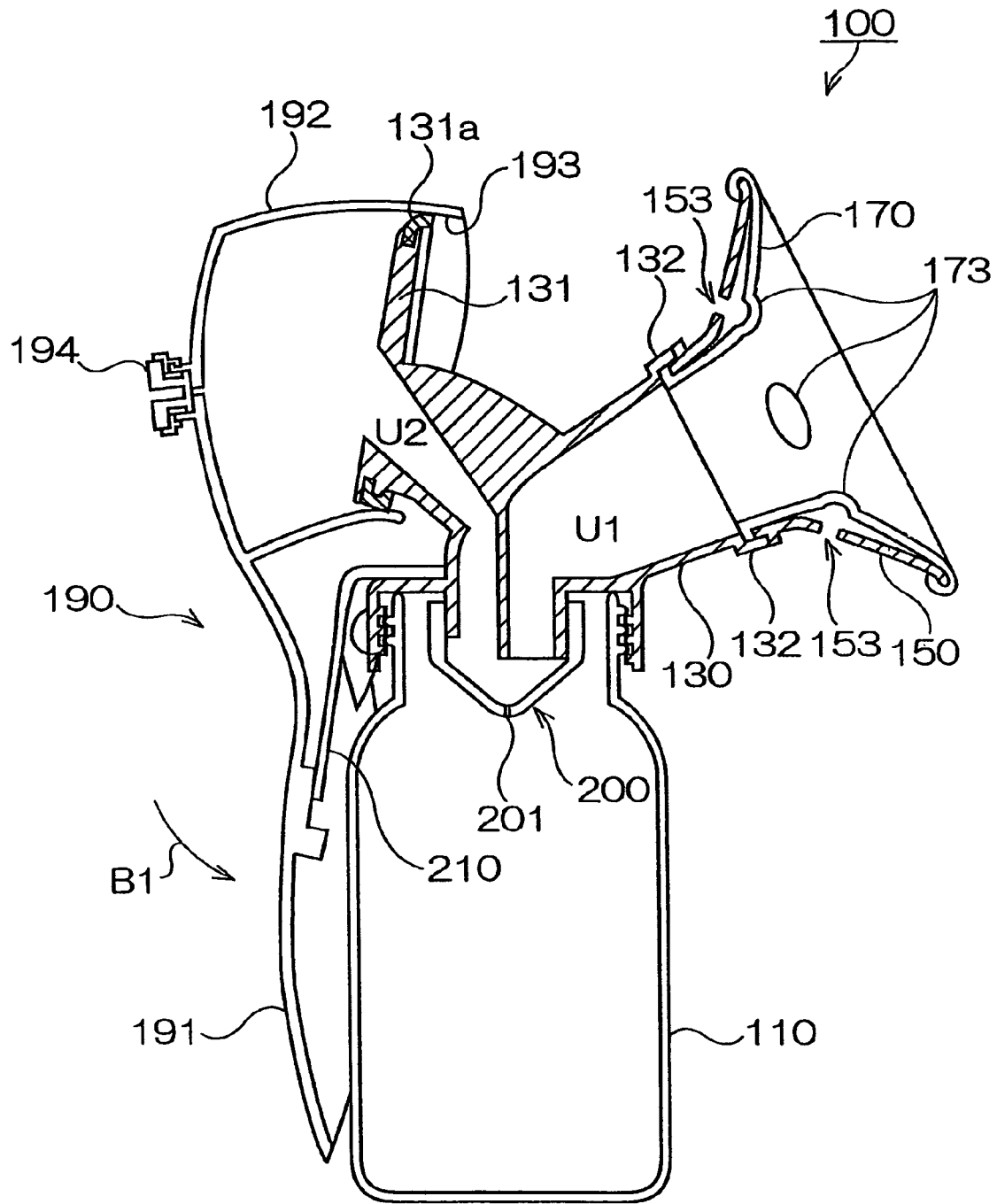
FIG. 5 schematically illustrates a condition where a lever shown in FIG. 2 is shifted in a direction indicated by an arrow B1.
Figure 6:
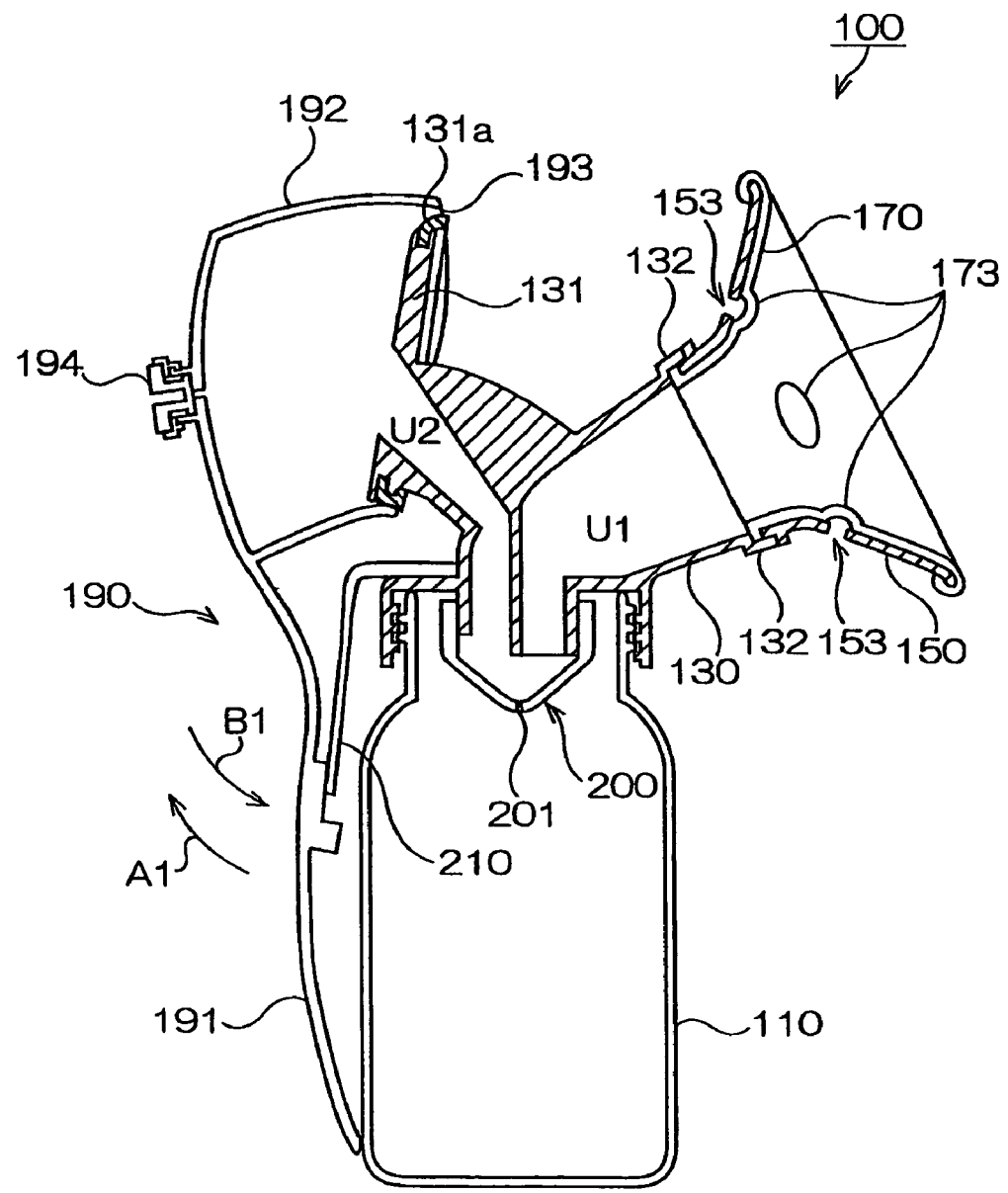
FIG. 6 schematically illustrates an air leak condition.
Figure 7:
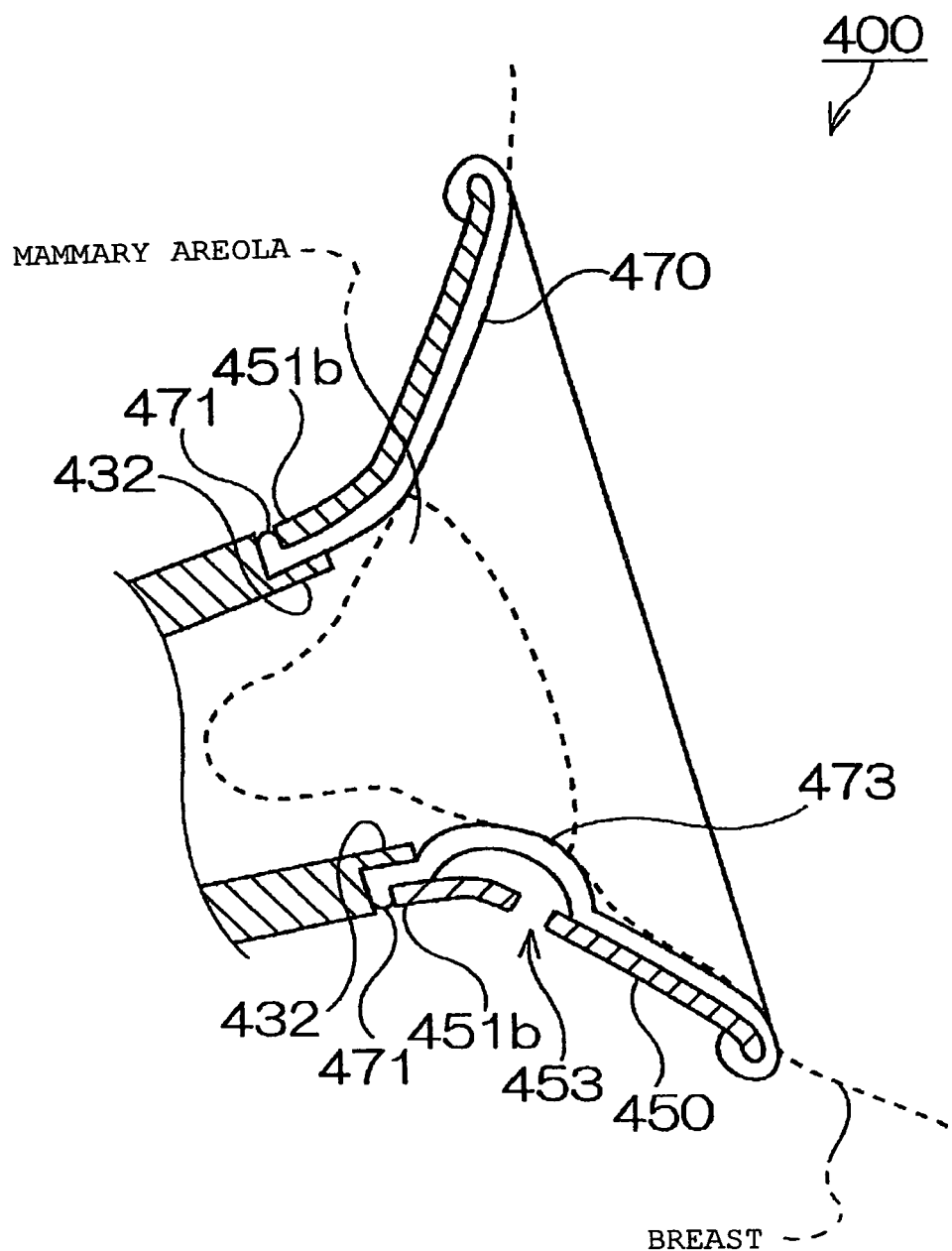
FIG. 7 schematically illustrates a manual breast pump in an example modified from the first embodiment.
Figure 8:
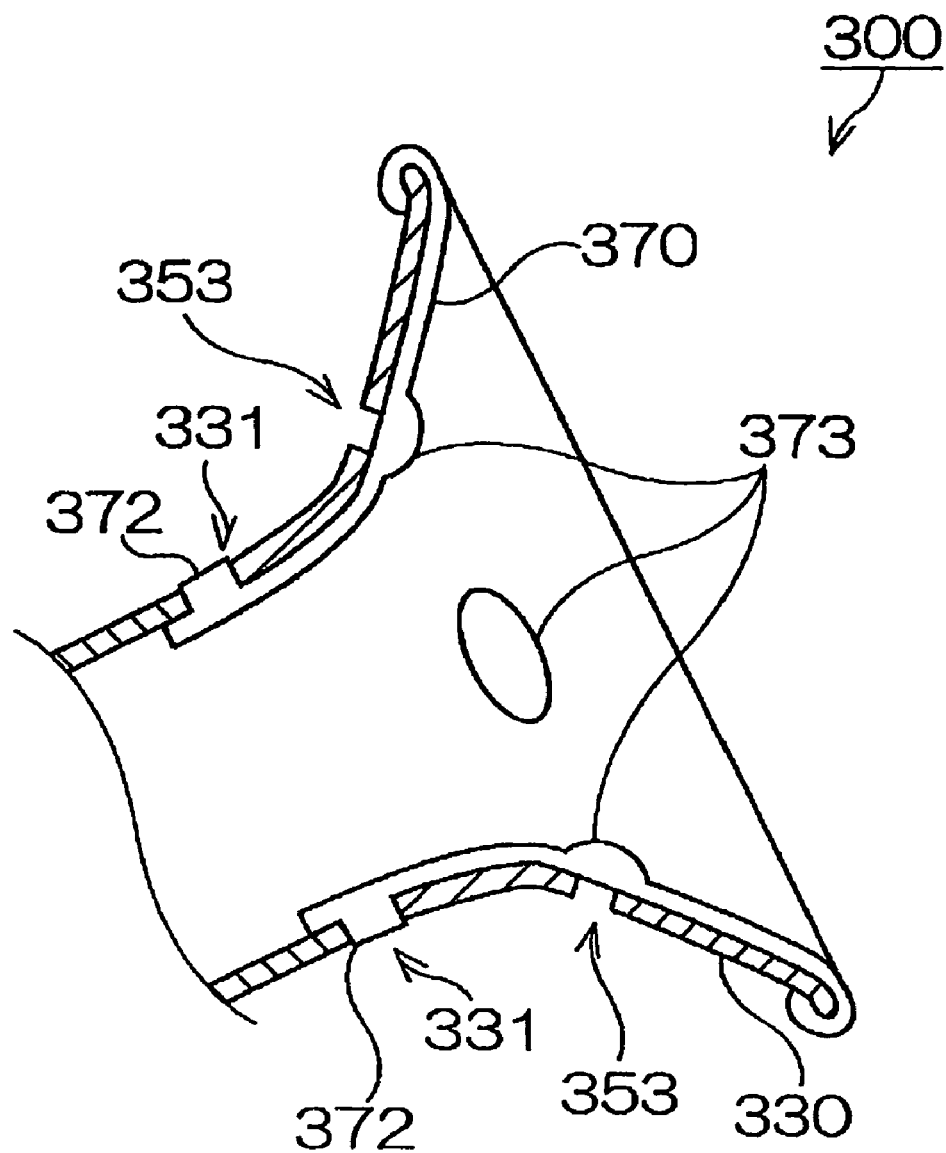
FIG. 8 schematically illustrates a main part of a manual breast pump in a second embodiment according to the invention.
Figure 9:
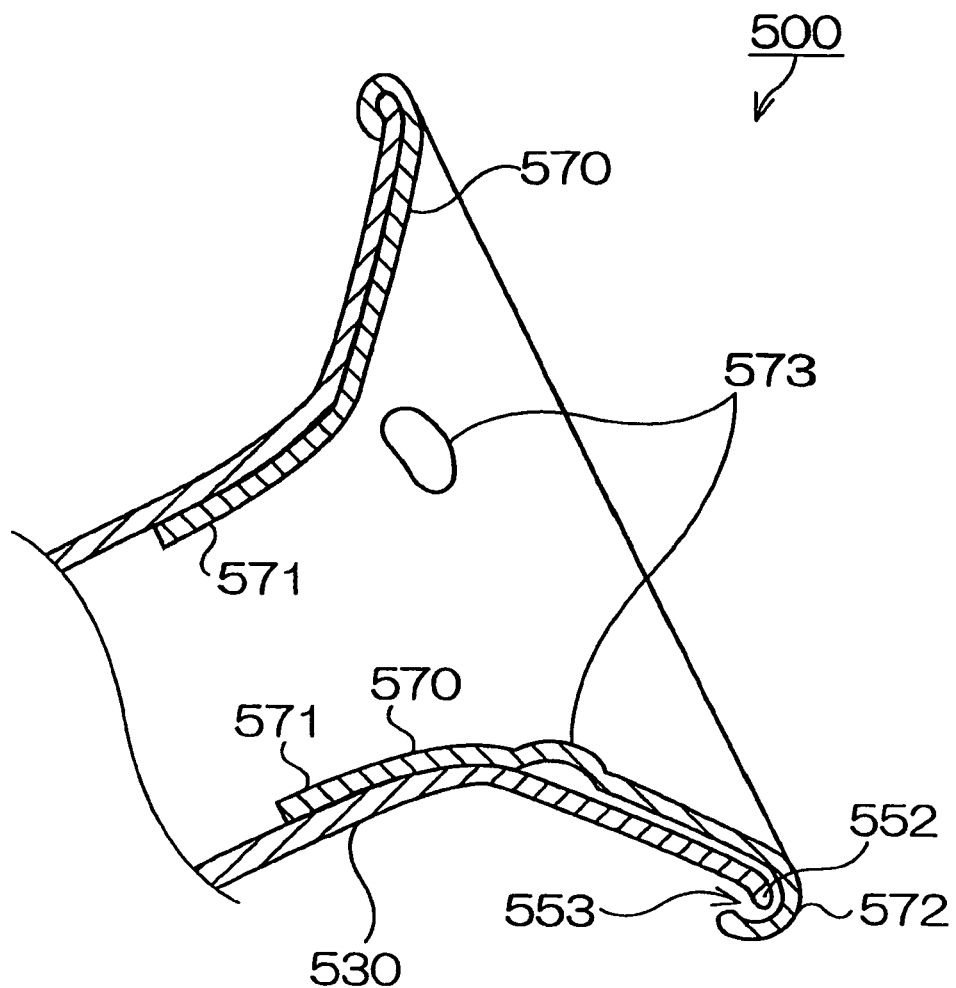
FIG. 9 schematically illustrates a manual breast pump in a third embodiment.
Figure 10:
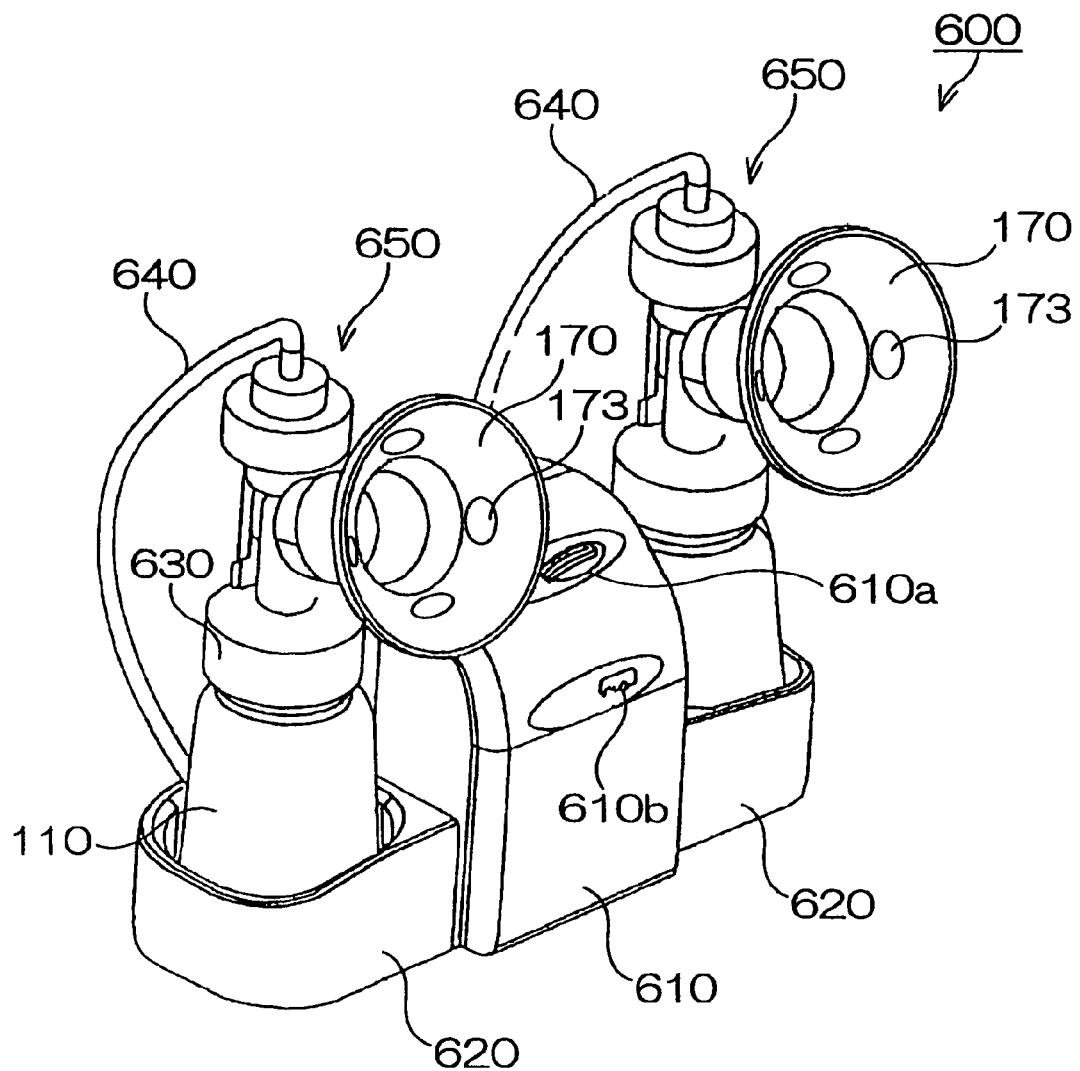
FIG. 10 schematically illustrates an electrically-powered breast pump in a fourth embodiment.
Figure 11:
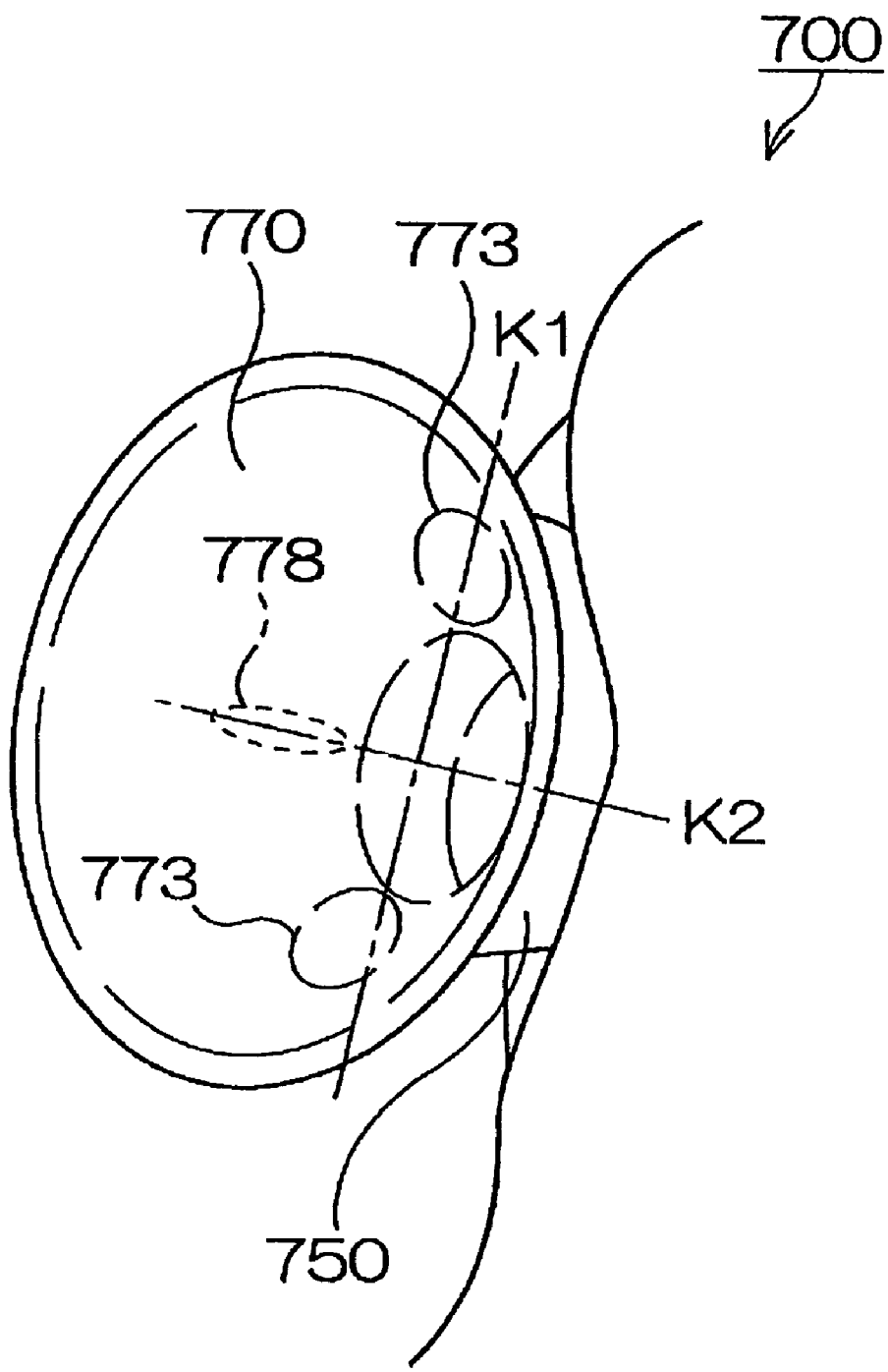
FIG. 11 is a perspective view schematically illustrating a horn member, a deformable member and other components as a main part of a manual breast pump in a fifth embodiment according to the invention.
Figure 12:
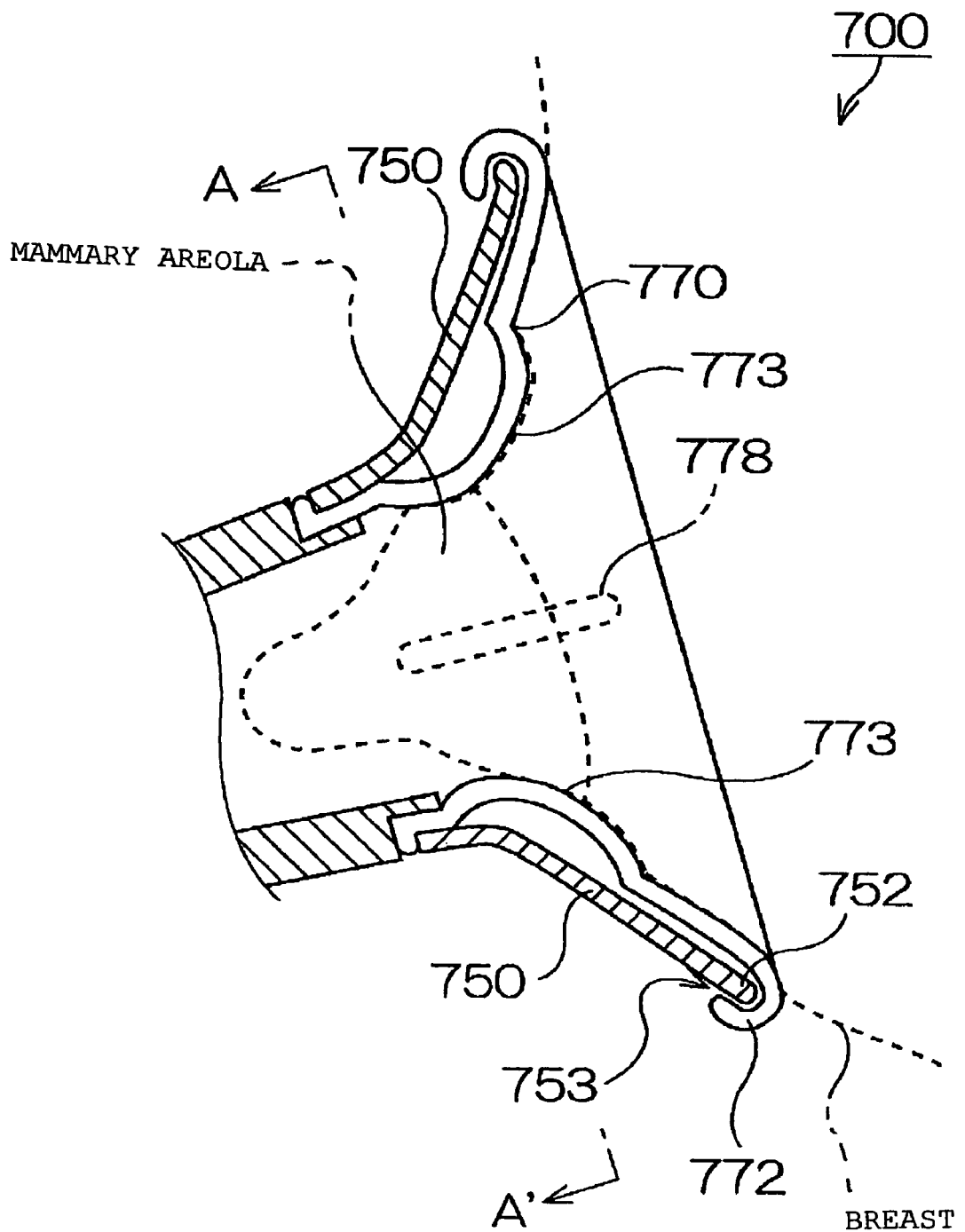
FIG. 12 is a cross-sectional view schematically illustrating the horn member, the deformable member and other components shown in FIG. 11.
Figure 13:
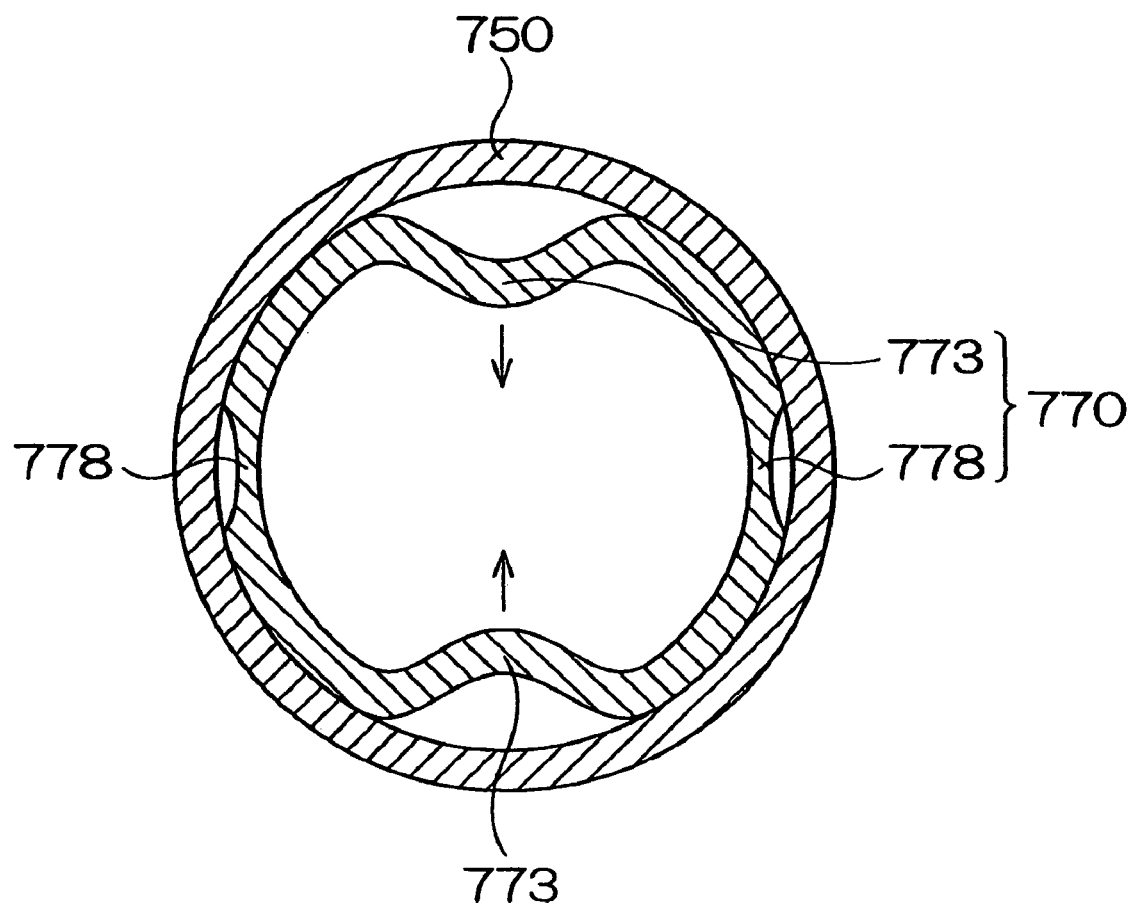
FIG. 13 is a schematic cross-sectional view of FIG. 12 taken along a line A-A'.

100, 300, 400, 500 Manual breast pump
110 Milk bottle
130, 330, 530, 630 Communicating portion
131 Fixed piston
131a Packing
132 Accommodating portion
150, 450 Horn member
151 Horn base end portion
151a Positioning concave
151b Base end side deformable member positioning portion
152, 552 Horn opening portion
153, 353, 453, 553 Vent opening
154 Curvature altering portion
170, 370, 470, 570 Deformable member
171, 571 Base end side detachable and attachable portion
172, 372, 572 Opening Side detachable and attachable portion
173, 373, 473, 573 Stimulating convex
173a Outer surface portion
190 Negative pressure generating means
191 Lever
192 Piston guide
193 Leak tip
194 Pressure regulating means
200 Valve
201 Leaf spring
331 Hole for attaching and detaching base end side
432 Connecting means
451b Base end side defmrable member positioning portion
471 Base end side detachable and attachable portion
600 Electrically-powered breast pump
610 Pump unit
610a Power source switch
610b Suction pressure controlling dial
620 Bottle holder
650 Bottle unit
640 Suction tube
S1 First opening
S2 Second opening
S3 Third opening
U1 First vent passage
U2 Second vent passage
U3 Third vent passage
778 Deformation guide portion

The invention claimed is:

1. A breast pump, comprising:
a milk container main body capable of accommodating sucked mother's milk;
a deformable member configured to provide a sealed space by contacting a breast;
a horn member disposed outside the deformable member;
an internal space pressure altering device that is configured to alternately provide a negative pressure condition and an atmospheric pressure condition in the sealed space; and
a communicating portion configured to connect the internal space pressure altering device and the sealed space,
wherein the horn member is configured such that it does not deform when internal pressure within the sealed space varies and has a base end disposed near the communicating portion, an inner surface, and an opening end disposed near an entrance through which the breast is inserted;
the deformable member is configured to cover the inner surface of the horn member, to deform when internal pressure within the sealed space varies, and has an attachable and detachable portion which is attachable to and detachable from the horn member;
the attachable and detachable portion has a base end side attachable and detachable portion configured to be fixed to the base end of the horn member and an opening side attachable and detachable portion configured to be fixed to the opening end of the horn member; and
the horn member has an atmospheric pressure condition creating structure configured to maintain an atmospheric pressure condition in a space between the deformable member and the horn member, wherein the atmospheric pressure condition creating structure is at least one vent opening formed by only the horn member so as to directly open the space between the deformable member and the horn member to atmosphere, and a first side of the at least one vent opening in the horn member is exposed directly to the space between the horn member and the deformable member, and an opposite side of the at least one vent opening in the horn member is exposed directly to atmosphere exterior to the breast pump, and the atmospheric pressure condition creating structure is configured to maintain an atmospheric pressure condition in the space between the deformable member and the horn member continuously during operation of the internal space pressure altering device during both a time at which the negative pressure condition is present in the sealed space and a time at which the atmospheric pressure condition is present in the sealed space, wherein the horn member includes a substantially conical shaped surface and the vent opening occupies a minority portion of the conical shaped surface.

2. A breast pump as set forth in claim 1, wherein the base end side attachable and detachable portion of the deformable member is disposed between the communicating portion and the base end of the horn member.

3. A breast pump as set forth in claim 2, wherein the deformable member has a stimulating convex projecting inwardly, and the stimulating convex is disposed between the base end side attachable and detachable portion and the opening side attachable and detachable portion.

4. A breast pump as set forth in claim 3, wherein a deformation guide portion that is configured to regulate a deformation direction of the deformable member is provided on the deformable member.

5. A breast pump as set forth in claim 4, wherein the stimulating convex is provided at a plurality of positions within the deformable member, and at least some of these stimulating convexes are opposed to each other on a first virtual line; and
the deformation guide portion is disposed on a second virtual line which crosses the first virtual line connecting the stimulating convexes provided in opposition to each other.

6. A breast pump as set forth in claim 2, wherein a deformation guide portion that is configured to regulate a deformation direction of the deformable member is provided on the deformable member.

7. A breast pump as set forth in claim 6, wherein
the deformable member has a stimulating convex projecting inwardly,
the stimulating convex is provided at a plurality of positions within the deformable member, and at least some of these stimulating convexes are opposed to each other on a first virtual line; and the deformation guide portion is disposed on a second virtual line which crosses the first virtual line connecting the stimulating convexes provided in opposition to each other.

8. The breast pump as set forth in claim 1, wherein the deformable member and horn member are configured such that a volume of the space between the deformable member and horn member changes when the internal space pressure altering device is operated.

9. A breast pump, comprising:
a milk container main body capable of accommodating sucked mother's milk;
a deformable member configured to provide a sealed space by contacting a breast;
a horn member disposed outside the deformable member;
an internal space pressure altering device that is configured to alternately provide a negative pressure condition and an atmospheric pressure condition in the sealed space; and
a communicating portion configured to connect the internal space pressure altering device and the sealed space,
wherein the horn member is configured such that it does not deform when internal pressure within the sealed space varies and has a base end disposed near the communicating portion, an inner surface, and an opening end disposed near an entrance through which the breast is inserted;
the deformable member is configured to cover the inner surface of the horn member, to deform when internal pressure within the sealed space varies, and has an attachable and detachable portion which is attachable to and detachable from the horn member;
the attachable and detachable portion has a base end side attachable and detachable portion configured to be fixed to the base end of the horn member and an opening side attachable and detachable portion configured to be fixed to the opening end of the horn member; and
the horn member has an atmospheric pressure condition creating structure configured to maintain an atmospheric pressure condition in a space between the deformable member and the horn member, wherein the atmospheric pressure condition creating structure is at least one vent opening formed by only the horn member so as to directly open the space between the deformable member and the horn member to atmosphere, and a first side of the at least one vent opening in the horn member is exposed directly to the space between the horn member and the deformable member, and an opposite side of the at least one vent opening in the horn member is exposed directly to atmosphere exterior to the breast pump, and the atmospheric pressure condition creating structure is configured to maintain an atmospheric pressure condition in the space between the deformable member and the horn member continuously during operation of the internal space pressure altering device during both a time at which the negative pressure condition is present in the sealed space and a time at which the atmospheric pressure condition is present in the sealed space, wherein the deformable member has a stimulating convex projecting inwardly, and the stimulating convex is disposed between the base end side attachable and detachable portion and the opening side attachable and detachable portion, and wherein the vent opening has a central axis and the stimulating convex is located at a position that intersects the central axis of the vent opening such that the stimulating convex moves relative to the horn member when the internal space pressure altering device is operated.

10. A breast pump as set forth in claim 9, wherein the stimulating convex of the deformable member is disposed in a vicinity of a curvature altering portion where a curvature of the base end of the horn member changes.

11. A breast pump as set forth in claim 10, wherein the base end side attachable and detachable portion of the deformable member is disposed between the communicating portion and the base end of the horn member.

12. A breast pump as set forth in claim 11, wherein a deformation guide portion that is configured to regulate a deformation direction of the deformable member is provided on the deformable member.

13. A breast pump as set forth in claim 12, wherein
the stimulating convex is provided at a plurality of positions within the deformable member, and at least some of these stimulating convexes are opposed to each other on a first virtual line; and
the deformation guide portion is disposed on a second virtual line which crosses the first virtual line connecting the stimulating convexes provided in opposition to each other.

14. A breast pump as set forth in claim 10, wherein a deformation guide portion that is configured to regulate a deformation direction of the deformable member is provided on the deformable member.

15. A breast pump as set forth in claim 14, wherein
the stimulating convex is provided at a plurality of positions within the deformable member, and at least some of these stimulating convexes are opposed to each other on a first virtual line; and
the deformation guide portion is disposed on a second virtual line which crosses the first virtual line connecting the stimulating convexes provided in opposition to each other.

16. A breast pump as set forth in claim 9, wherein a deformation guide portion that is configured to regulate a deformation direction of the deformable member is provided on the deformable member.

17. A breast pump as set forth in claim 16, wherein
the stimulating convex is provided at a plurality of positions within the deformable member, and at least some of these stimulating convexes are opposed to each other on a first virtual line; and
the deformation guide portion is disposed on a second virtual line which crosses the first virtual line connecting the stimulating convexes provided in opposition to each other.

18. A breast pump, comprising:
a milk container main body capable of accommodating sucked mother's milk;
a deformable member configured to provide a sealed space by contacting a breast;
a horn member disposed outside the deformable member;
an internal space pressure altering device that is configured to alternately provide a negative pressure condition and an atmospheric pressure condition in the sealed space; and
a communicating portion configured to connect the internal space pressure altering device and the sealed space,
wherein the horn member is configured such that it does not deform when internal pressure within the sealed space varies and has a base end disposed near the communicating portion, an inner surface, and an opening end disposed near an entrance though which the breast is inserted;

the deformable member is configured to cover the inner surface of the horn member, to deform when internal pressure within the sealed space varies, and has an attachable and detachable portion which is attachable to and detachable from the horn member;

the attachable and detachable portion has a base end side attachable and detachable portion configured to be fixed to the base end of the horn member and an opening side attachable and detachable portion configured to be fixed to the opening end of the horn member;

the horn member has an atmospheric pressure condition creating structure configured to maintain an atmospheric pressure condition in a space between the deformable member and the horn member, wherein the atmospheric pressure condition creating structure includes a vent opening in the horn member, and the vent opening occupies a minority portion of the horn member; and wherein a deformation guide portion that is configured to regulate a deformation direction of the deformable member is provided on the deformable member, the deformation guide portion having a thinner wall than a wall of the deformable member, and the atmospheric pressure condition creating structure is configured to maintain an atmospheric pressure condition in the space between the deformable member and the horn member continuously during operation of the internal space pressure altering device during both a time at which the negative pressure condition is present in the sealed space and a time at which the atmospheric pressure condition is present in the sealed space.

19. A breast pump as set forth in claim 18, wherein the deformable member has a stimulating convex projecting inwardly, and the stimulating convex is disposed between the base end side attachable and detachable portion and the opening side attachable and detachable portion.

20. A breast pump as set forth in claim 19, wherein the stimulating convex is provided at a plurality of positions within the deformable member, and at least some of these stimulating convexes are opposed to each other on a first virtual line; and the deformation guide portion is disposed on a second virtual line which crosses the first virtual line connecting the stimulating convexes provided in opposition to each other.

21. A breast pump, comprising:

a milk container main body capable of accommodating sucked mother's milk;

a deformable member configured to provide a sealed space by contacting a breast;

a horn member disposed outside the deformable member;

an internal space pressure altering device that is configured to alternately provide a negative pressure condition and an atmospheric pressure condition in the sealed space: and a communicating portion configured to connect the internal space pressure altering device and the sealed space, wherein the horn member is configured such that it does not deform when internal pressure within the sealed space varies and has a base end disposed near the communicating portion, an inner surface, and an opening end disposed near an entrance though which the breast is inserted;

the deformable member is configured to cover the inner surface of the horn member, to deform when internal pressure within the sealed space varies, and has an attachable and detachable portion which is attachable to and detachable from the horn member;

the attachable and detachable portion has a base end side attachable and detachable portion configured to be fixed to the base end of the horn member and an opening side attachable and detachable portion configured to be fixed to the opening end of the horn member; and the horn member has an atmospheric pressure condition creating structure configured to maintain an atmospheric pressure condition in a space between the deformable member and the horn member, wherein the atmospheric pressure condition creating structure is at least one vent opening formed by only the horn member so as to directly open the space between the deformable member and the horn member to atmosphere, and a first side of the at least one vent opening in the horn member is exposed directly to the space between the horn member and the deformable member, and an opposite side of the at least one vent opening in the horn member is exposed directly to atmosphere exterior to the breast pump, and the atmospheric pressure condition creating structure is configured to maintain an atmospheric pressure condition in the space between the deformable member and the horn member continuously during operation of the internal space pressure altering device during both a time at which the negative pressure condition is present in the sealed space and a time at which the atmospheric pressure condition is present in the sealed space, wherein the deformable member has a stimulating convex projecting inwardly, and the stimulating convex is disposed between the base end side attachable and detachable portion and the opening side attachable and detachable portion, wherein the vent opening is smaller than the stimulating convex.

* * * * *